United States Patent
Van Tol et al.

(10) Patent No.: US 10,342,568 B2
(45) Date of Patent: Jul. 9, 2019

(54) ULTRASONIC SURGICAL DEVICE AND METHOD FOR DETECTION OF ATTACHMENT OF ULTRASONIC PROBE

(71) Applicant: COVIDIEN LP, Mansfield, MA (US)

(72) Inventors: David J. Van Tol, Boulder, CO (US); Robert B. Stoddard, Steamboat Springs, CO (US)

(73) Assignee: COVIDIEN LP, Mansfield, MA (US)

( * ) Notice: Subject to any disclaimer, the term of this patent is extended or adjusted under 35 U.S.C. 154(b) by 418 days.

(21) Appl. No.: 15/161,451

(22) Filed: May 23, 2016

(65) Prior Publication Data

US 2016/0374711 A1    Dec. 29, 2016

Related U.S. Application Data

(60) Provisional application No. 62/183,333, filed on Jun. 23, 2015.

(51) Int. Cl.
*A61B 18/12* (2006.01)
*A61B 17/32* (2006.01)
(Continued)

(52) U.S. Cl.
CPC ........... *A61B 17/320092* (2013.01); *A61B 17/320068* (2013.01); *A61B 90/08* (2016.02); *A61N 7/00* (2013.01); *A61B 2017/00017* (2013.01); *A61B 2017/00473* (2013.01); *A61B 2017/00725* (2013.01); *A61B 2018/00178* (2013.01);
(Continued)

(58) Field of Classification Search
CPC ............ A61B 17/320092; A61B 90/08; A61B 17/320068; A61B 2090/0808; A61B 2018/00178; A61B 2017/00725; A61B 2017/00473; A61B 2018/00845; A61B 2090/0812; A61B 2017/00017; A61N 7/00

See application file for complete search history.

(56) References Cited

U.S. PATENT DOCUMENTS

6,537,291 B2 *   3/2003   Friedman ........ A61B 17/320068
                                                  606/169
6,662,127 B2    12/2003   Wiener et al.
(Continued)

FOREIGN PATENT DOCUMENTS

EP    1199042 A2    4/2002
EP    1199043 A2    4/2002

OTHER PUBLICATIONS

European Search Report in corresponding EP Application No. 16175673.9, dated Nov. 22, 2016, 8 pages.

*Primary Examiner* — Jaymi E Della (57) ABSTRACT

The ultrasonic surgical device includes a power source configured to generate power, an ultrasonic transducer having a first resonant frequency, the ultrasonic transducer electrically coupled to the power source and configured to generate ultrasonic motion in response to the generated power, an ultrasonic probe configured to be mechanically couplable to the ultrasonic transducer, the ultrasonic transducer and the ultrasonic probe having a second resonant frequency when the ultrasonic probe is coupled to the ultrasonic transducer, and a controller configured to determine whether the ultrasonic probe is properly coupled to the ultrasonic transducer based on the first resonant frequency and the second resonant frequency.

5 Claims, 6 Drawing Sheets

(51) Int. Cl.
  *A61B 90/00* (2016.01)
  *A61N 7/00* (2006.01)
  A61B 18/00 (2006.01)
  A61B 17/00 (2006.01)

(52) U.S. Cl.
  CPC ............... *A61B 2018/00845* (2013.01); *A61B 2018/00994* (2013.01); *A61B 2090/0808* (2016.02); *A61B 2090/0812* (2016.02)

(56) References Cited

U.S. PATENT DOCUMENTS

| | | |
|---|---|---|
| 6,678,621 B2 | 1/2004 | Wiener et al. |
| 7,546,781 B2 | 6/2009 | Takahashi |
| 2007/0167881 A1* | 7/2007 | Takahashi ...... A61B 17/320068 601/2 |
| 2009/0143798 A1 | 6/2009 | Smith et al. |
| 2010/0004558 A1* | 1/2010 | Frankhouser ........ A61B 10/025 600/567 |
| 2012/0078139 A1 | 3/2012 | Aldridge et al. |
| 2014/0276754 A1* | 9/2014 | Gilbert .................. A61B 18/18 606/33 |
| 2015/0148830 A1 | 5/2015 | Stulen et al. |

* cited by examiner

ULTRASONIC SURGICAL DEVICE AND METHOD FOR DETECTION OF ATTACHMENT OF ULTRASONIC PROBE

CROSS REFERENCE TO RELATED APPLICATION

The present application claims the benefit of and priority to U.S. Provisional Application Ser. No. 62/183,333, filed on Jun. 23, 2015, the entire contents of which are incorporated herein by reference.

BACKGROUND

Technical Field

The present disclosure relates to an ultrasonic surgical device for verifying integrity of mechanical coupling between an ultrasonic probe and an ultrasonic transducer of the ultrasonic surgical device. More specifically, the present disclosure relates to an ultrasonic surgical device configured to detect proper attachment of an ultrasonic probe to an ultrasonic transducer.

Background of Related Art

Ultrasonic surgical devices have been demonstrated to provide hemostasis and efficient dissection of tissue with minimum lateral thermal damage and low smoke generation. Unlike electrosurgical devices, which require electrical current to flow through a patient, ultrasonic surgical devices operate by applying mechanical motion through an ultrasonic probe using an ultrasonic transducer that is driven at a resonant frequency. Thus, the ultrasonic surgical devices do not harm tissue due to overexposure of electrical current being passed through the tissue.

However, when the ultrasonic transducer is not properly connected or attached to the ultrasonic probe, the ultrasonic transducer cannot deliver desired mechanical motion so as to obtain desired therapeutic effects to tissue. Alternatively, improper attachment of the ultrasonic probe may render the ultrasonic device inoperable as the ultrasonic transducer would be incapable of generating sufficient mechanical motion at the resonant frequency. Thus, there is a need for determining and analyzing the quality and/or integrity of the connection of the ultrasonic probe and the ultrasonic transducer as well as for notifying a clinician of the improper connection.

SUMMARY

The present disclosure provides ultrasonic surgical devices, which include an ultrasonic transducer and an ultrasonic probe and are configured to analyze integrity of a mechanical coupling of the ultrasonic probe to the ultrasonic transducer. The present disclosure also provides a method for analyzing the connection between the ultrasonic probe and the ultrasonic transducer.

The ultrasonic surgical device includes a power source configured to generate power, an ultrasonic transducer having a first resonant frequency, the ultrasonic transducer electrically coupled to the power source and configured to generate ultrasonic motion in response to the generated power, an ultrasonic probe configured to be mechanically couplable to the ultrasonic transducer, the ultrasonic transducer and the ultrasonic probe having a second resonant frequency when the ultrasonic probe is coupled to the ultrasonic transducer, and a controller configured to determine whether the ultrasonic probe is properly coupled to the ultrasonic transducer based on the first resonant frequency and the second resonant frequency.

In an aspect, the power source includes a battery configured to generate a direct current (DC) power, and an inverter electrically coupled to the battery and configured to invert the DC power to an alternating current (AC) power having an ultrasonic frequency.

In another aspect, the power source further includes an alternating current (AC) power source configured to supply AC power having a low frequency, a converter configured to convert the AC power to a direct current (DC) power, an amplifier configured to amplify an amplitude of the DC power, and an inverter configured to invert the amplified DC power to an AC power having an ultrasonic frequency.

In another aspect, the controller further calculates a difference between the first resonant frequency and the second resonant frequency, and determines whether the ultrasonic probe is properly coupled to the ultrasonic transducer based on a comparison of the difference and a predetermined threshold. The controller determines that the ultrasonic probe is properly coupled to the ultrasonic transducer based on the difference being above the predetermined threshold.

In yet another aspect, the ultrasonic surgical device further includes a display configured to display a warning in response the determination of proper coupling between the ultrasonic probe and the ultrasonic transducer.

In still another aspect, the ultrasonic surgical device further includes an audio output port configured to output an audible alert in response to the determination of proper coupling between the ultrasonic probe and the ultrasonic transducer.

The method for detecting a proper connection between an ultrasonic probe and an ultrasonic transducer of an ultrasonic surgical device includes obtaining a first resonant frequency of the ultrasonic transducer, obtaining a second resonant frequency of the ultrasonic transducer and the ultrasonic probe when the ultrasonic probe is coupled to the ultrasonic transducer, and determining whether the ultrasonic probe is properly coupled to the ultrasonic transducer based on the first resonant frequency and the second resonant frequency.

The determination of proper coupling of the ultrasonic probe includes calculating a difference between the first resonant frequency and the second resonant frequency, and determining whether the difference is greater than a predetermined threshold. The difference not being greater than the predetermined threshold is indicative of the ultrasonic probe being improperly coupled to the ultrasonic transducer. The differences being greater than the predetermined threshold is indicative of the ultrasonic probe being properly coupled to the ultrasonic transducer.

In an aspect, determination of proper coupling of the ultrasonic probe further includes displaying a warning of improper coupling between the ultrasonic transducer and the ultrasonic probe on a display of the ultrasonic surgical device in response to a determination that the difference is not greater than the predetermined threshold.

In another aspect, the determination of proper coupling of the ultrasonic probe further includes generating an audible alert of improper coupling between the ultrasonic transducer and the ultrasonic probe in response to a determination that the difference is not greater than the predetermined threshold.

In another aspect, determination of proper coupling of the ultrasonic probe further includes re-connecting the ultrasonic probe to the ultrasonic transducer in response to a determination that the difference is not greater than the predetermined threshold.

In yet another aspect, determination of proper coupling of the ultrasonic probe further includes adjusting a physical property of the ultrasonic probe in response to a determination that the difference is not greater than the predetermined threshold. The physical property of the ultrasonic probe is a length of a waveguide of the ultrasonic probe.

BRIEF DESCRIPTION OF THE DRAWINGS

The present disclosure may be understood by reference to the accompanying drawings, when considered in conjunction with the subsequent, detailed description, in which.

DETAILED DESCRIPTION

Generally, the present disclosure provides an ultrasonic surgical device for detecting a defect in a connection between an ultrasonic transducer and an ultrasonic probe of an ultrasonic surgical device. The ultrasonic transducer is configured to generate ultrasonic mechanical motion at its resonant frequency. The ultrasonic surgical device also includes a processor that is programmed to detect an improper connection between the ultrasonic transducer and the ultrasonic probe based on the changes in the resonant frequency of the ultrasonic transducer.

A pulse-width modulation (PWM) amplitude control is employed to regulate the mechanical motion of the ultrasonic probe and to provide different levels of power for treating tissue. Further, a proportional-integral (PI) controller is included to obtain a rapid transient response to changes in load and to maintain stable surgical operations.

The ultrasonic surgical device also includes two control loops, which may be embodied in hardware and/or software executed by the processor, to control the ultrasonic mechanical motion of the ultrasonic transducer, which is energized by a DC power source. The first loop is an amplitude control loop configured to control average power delivered to the ultrasonic transducer and to regulate the longitudinal mode displacement and includes a closed-loop feedback control. The second loop generates an AC signal from the DC power supplied to the ultrasonic transducer and automatically tracks the resonant frequency of the ultrasonic transducer. The second control loop includes a band-pass filter oscillator. By using the first and second control loops, the ultrasonic surgical device provides regulated ultrasonic mechanical motion at resonant frequency sufficient to treat tissue in accordance with embodiments of this disclosure.

Figure 1A:
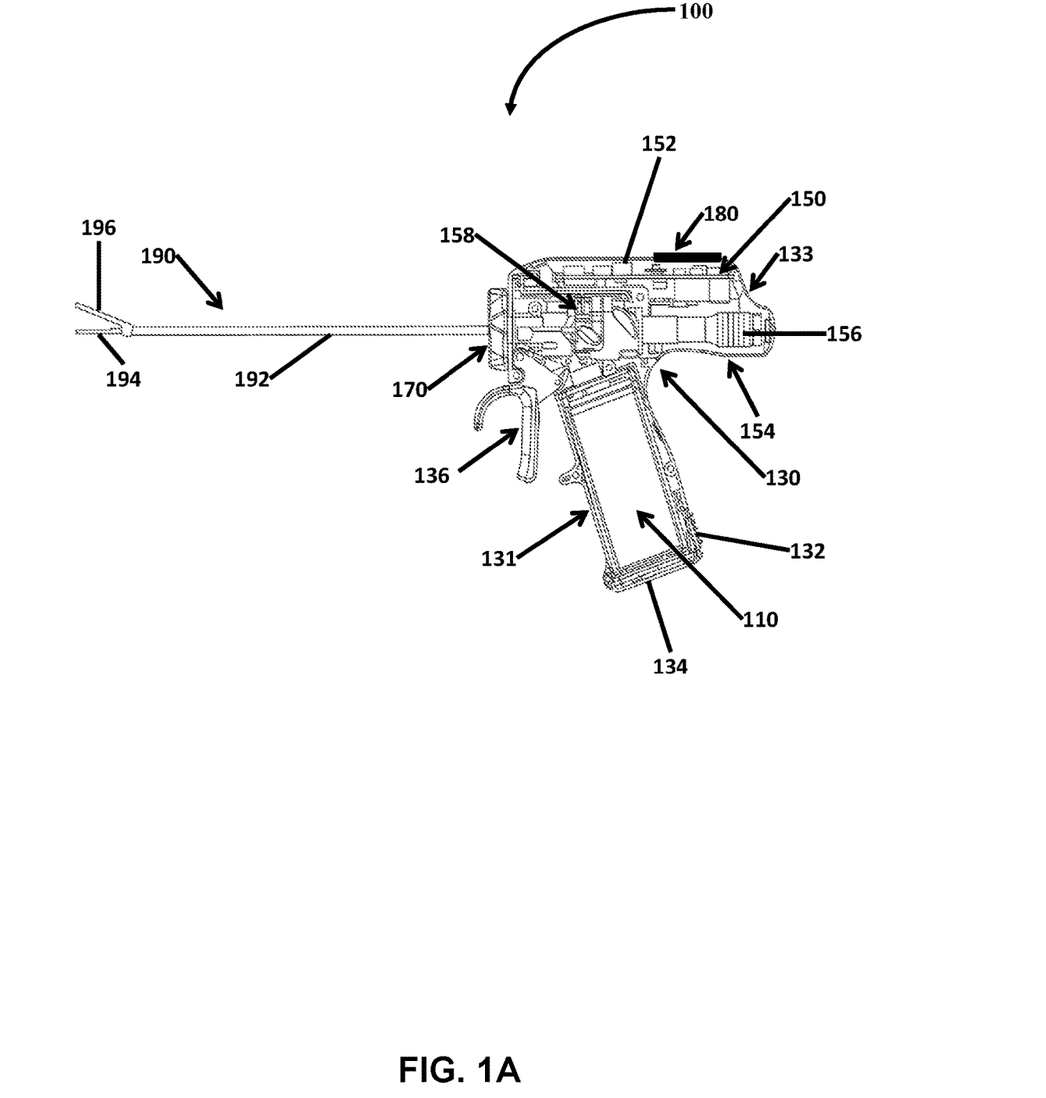
FIG. 1A is a side elevation view of an ultrasonic surgical device in accordance with embodiments of the present disclosure.
Figure 1B:
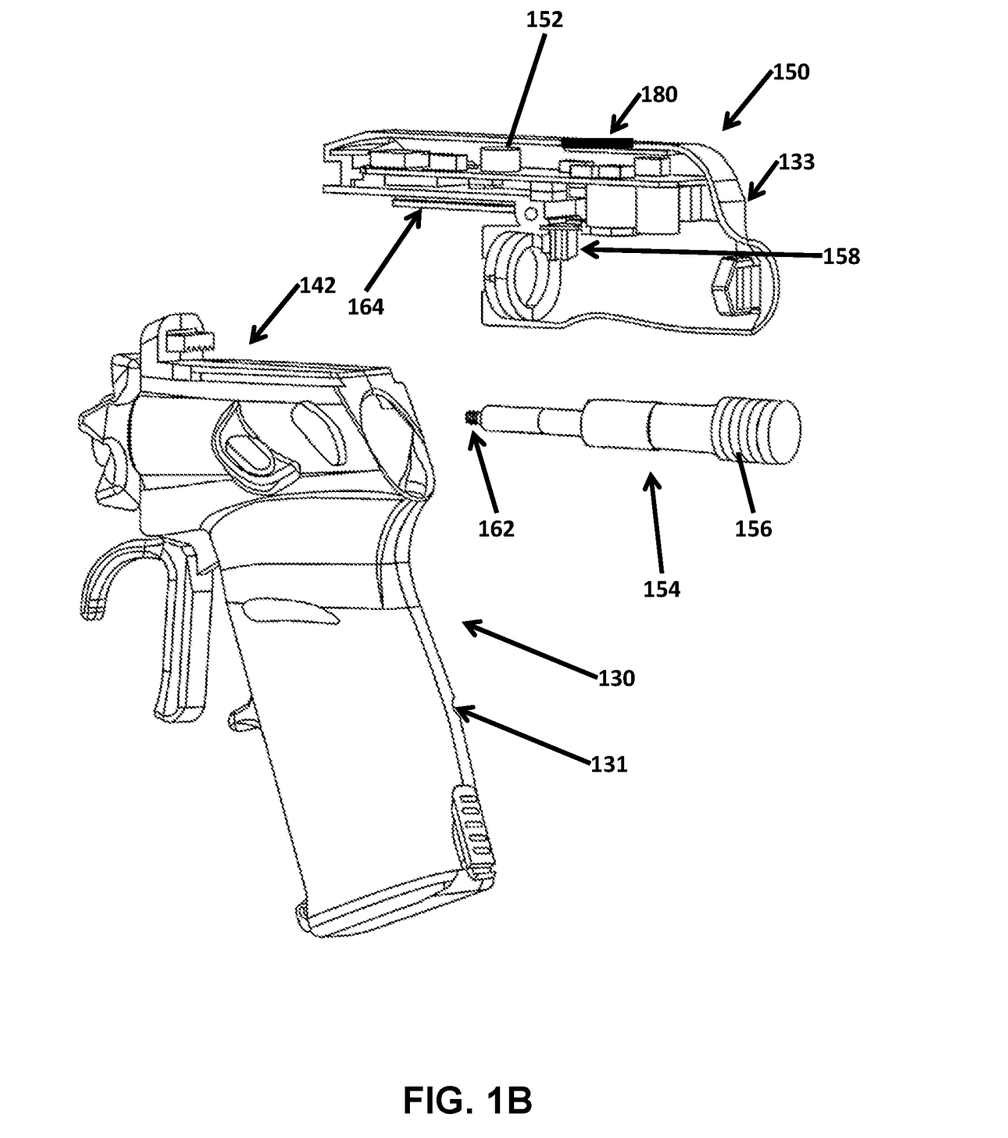
FIG. 1B is a perspective view of parts separated, which shows the left side of a handle, an ultrasonic transducer, and the right side of the ultrasonic surgical device of FIG. 1A in accordance with embodiments of the present disclosure.

With reference to FIGS. 1A-1B, an ultrasonic surgical device 100 for treating tissue is illustrated. The ultrasonic surgical device 100 includes a power source 110, a housing 130, an ultrasonic transducer 150, and an ultrasonic probe 190. The power source 110 provides DC power to the ultrasonic transducer 150. In an aspect, the power source 110 may be a battery that directly provides DC power. In a further aspect, the power source 110 may be insertable or integrated into the housing 130 so that the ultrasonic surgical device 100 may be portably carried without disturbances of any cable. In yet another aspect, the power source 110 may be rechargeable so that the power source 110 may be reusable.

In another aspect, the power source 110 may include a converter that is connected to an alternating current (AC) power source and converts the AC power to DC power. The AC power source may be of a relatively low frequency, such as about 60 hertz (Hz), while the ultrasonic surgical device 100 may operate at a higher frequency, such as 55.5 kilo hertz (kHz). Thus, the power source 110 may convert the low frequency AC power to DC power so that the DC power may then be inverted to AC power having a frequency suitable to cause the ultrasonic transducer 150 to generate ultrasonic mechanical motion.

With continued reference to FIGS. 1A and 1B, the housing 130 includes a handle portion 131 having a compartment 132, which houses the power source 110, and a power source door 134 that secures the power source 110 within the compartment 132. In an aspect, the power source door 134 may be configured to form a water-tight seal between the interior and the exterior of the compartment 132.

The housing 130 also includes a cover 133, which houses the ultrasonic transducer 150 and an output device 180. The ultrasonic transducer 150 includes a generator assembly 152 and a transducer assembly 154, having a transducer body 156 and a locking portion 162. The generator assembly 152 is electrically coupled to the transducer assembly 154 via a pair of contacts 158.

With reference to FIG. 1B, the ultrasonic transducer 150 is illustrated as being separate from the cover 133. When the ultrasonic transducer 150 is inserted into and assembled with the cover 133, the pair of contacts 158 is connected to the round groove of the ultrasonic transducer 150 so that the rotational movement of the transducer body 156 does not disrupt the connection between the transducer body 156 and the generator assembly 152. Thus, the transducer body 156 is capable of freely rotating within the housing 130.

The output device 180 outputs information about the ultrasonic surgical device 100 or a status of the mechanical coupling between the ultrasonic probe 190 and the ultrasonic transducer 150. The output device 180 may also display a warning that the ultrasonic probe 190 is not properly connected to the ultrasonic transducer 150.

In another aspect, the output device 180 may be a speaker configured to output audible tones denoting proper or improper connection of the ultrasonic probe 190 to the ultrasonic transducer 150. In yet another aspect, the output device 180 may include one or more light emitting devices, configured to emit lights of various duration, pulses, and colors indicating the status of the mechanical coupling between the ultrasonic probe 190 and the ultrasonic transducer 150.

The handle portion 131 further includes a trigger 136. When the trigger 136 is actuated, the power source 110 provides energy to the ultrasonic transducer 150 so that the ultrasonic transducer 150 is powered to generate ultrasonic mechanical motion of the ultrasonic probe 190. As the trigger 136 is released, the power supply to the ultrasonic transducer 150 is terminated.

The generator assembly 152 receives the DC power from the power source 110 and generates AC signals having an ultrasonic frequency. The generator assembly 152 may be capable of generating signals having a frequency based on a desired mode of operation, which may be different from the resonant frequency of the ultrasonic transducer 150.

In an aspect, the generator assembly 152 may generate AC signals having a relatively wide range of frequencies (e.g., broadband signals) or a relatively small range of frequencies (e.g., narrowband signals). The broadband AC signals may be used to detect or set a resonant frequency and an anti-resonant frequency of the ultrasonic transducer 150. Presence or absence of the ultrasonic probe 190 and/or quality of the connection between the ultrasonic probe 190 and the ultrasonic transducer 150 may be analyzed based on the resonant and anti-resonant frequencies as described in further detail below.

The transducer body 156 of the transducer assembly 154 receives the AC signal generated by the generator assembly 152 and generates ultrasonic mechanical motion within the ultrasonic probe 190 based on the amplitude and the frequency of the generated AC signal. The transducer body 156 includes a piezoelectric material, which converts the generated AC signal into ultrasonic mechanical motion. The transducer body 156 may be based on an electrical oscillator model having an inductor and a capacitor, which oscillates between charging and discharging electrical energy. This oscillation model for the transducer body 156 is described further in detail below with respect to FIG. 4.

The ultrasonic surgical device 100 also includes a spindle 170, which is coupled to the ultrasonic probe 190 and allows for rotation of the ultrasonic probe 190 about its longitudinal axis. The ultrasonic probe 190 is attached to the housing and is mechanically connected to the ultrasonic transducer 150 via the locking portion 162 such that as the spindle 170 is rotated about the longitudinal axis defined by the ultrasonic probe 190, the ultrasonic probe 190 and the ultrasonic transducer 150 are also rotated correspondingly without affecting the connection between the ultrasonic transducer 150 and the ultrasonic probe 190. Additionally, as the spindle 170 is rotated, the ultrasonic transducer 150 may be also rotated along with the ultrasonic probe 190.

FIG. 1B illustrates the ultrasonic transducer 150 separated from the handle portion 131 of the housing 130 of FIG. 1A. The ultrasonic transducer 150 includes a slidable first connector 164 and the handle portion 131 of the housing 130 includes a second connector 142 configured and dimensioned to engage the slidable first connector 164 allowing for selective engagement of the ultrasonic transducer 150 with the handle portion 131.

The locking portion 162 physically and/or mechanically locks the ultrasonic probe 190 to the ultrasonic transducer 150. The locking portion 162 maintains physical contact between the ultrasonic probe 190 and the transducer body 156 as the ultrasonic probe 190 is rotated. The locking portion 162 conveys the ultrasonic mechanical motion from the transducer body 156 to the ultrasonic probe 190 without losing the connection. In an aspect, the locking portion 162 may be a male connector and the ultrasonic probe 190 may include a counterpart female connector.

The ultrasonic probe 190 may include an end effector suitable for sealing tissue. The ultrasonic probe 190 includes a waveguide 192, a blade 194 extending from the waveguide 192, and a jaw member 196. The ultrasonic probe 190 is mechanically coupled to the transducer body 156 via the locking portion 162.

The jaw member 196 may be formed as a pivoting arm configured to grasp and/or clamp tissue between the jaw member 196 and the blade 194. When the jaw member 196 and the blade 194 grasp tissue and the blade 194 conveys the ultrasonic mechanical motion, temperature of the grasped tissue between the blade 194 and the jaw member 196 increases due to the ultrasonic mechanical motion. This motion in turn treats, e.g., cuts and/or seals, tissue.

In instances when the ultrasonic probe 190 is not properly attached to the ultrasonic transducer 150, the ultrasonic mechanical motion generated by the ultrasonic transducer 150 is not optimally delivered to the ultrasonic probe 190. As a result, the ultrasonic surgical device 100 may malfunction, which may result in improper treatment of the tissue. The ultrasonic surgical device 100 according to the present disclosure is configured to determine whether the ultrasonic probe 190 is properly connected to the ultrasonic transducer 150 to ensure proper operation of the ultrasonic probe 190.

Figure 2:
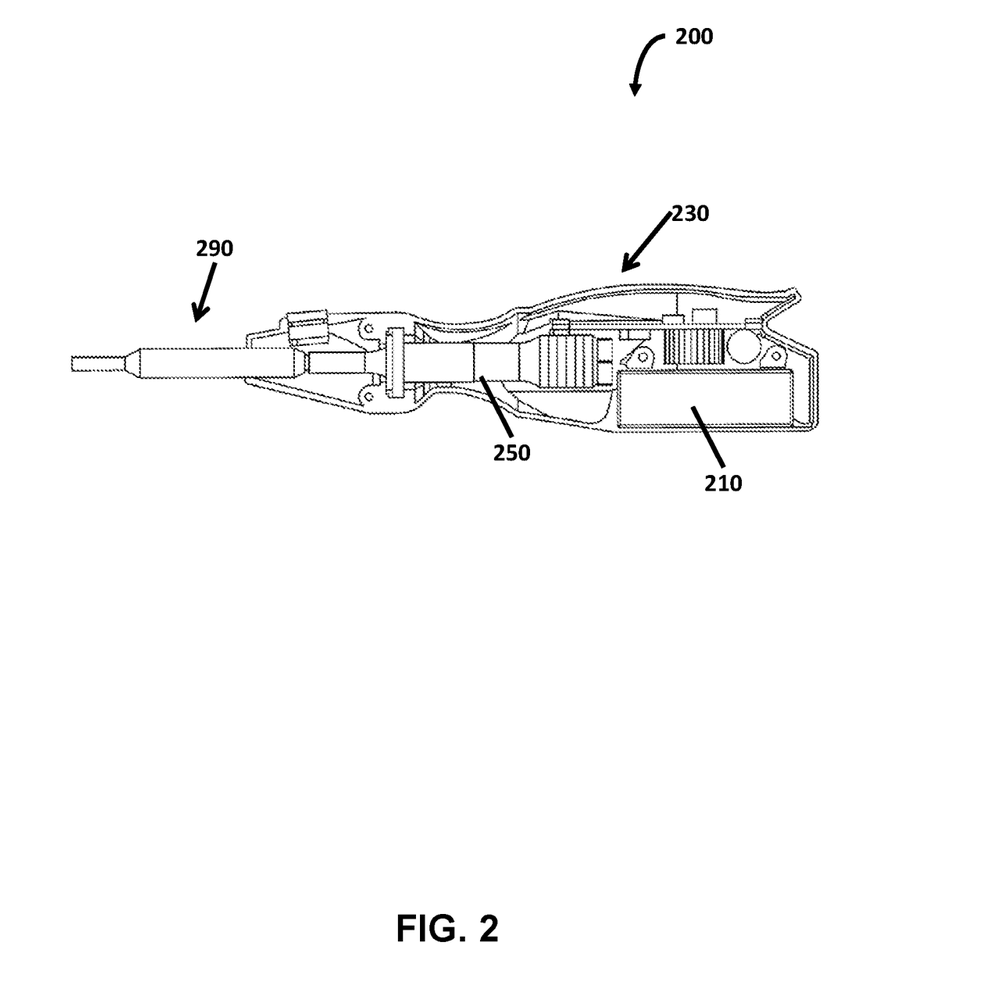
FIG. 2 is a side cross-sectional elevation view of an ultrasonic surgical pen in accordance with embodiments of the present disclosure.

FIG. 2 shows an ultrasonic surgical pen 200, which is another illustrative embodiment of the ultrasonic surgical device 100 of FIG. 1A. The ultrasonic surgical pen 200 includes a power source 210, the housing 230, the ultrasonic transducer 250, and the ultrasonic probe 290. The power source 210, the housing 230, and the ultrasonic transducer 250 of the ultrasonic surgical pen 200 are substantially similar to the power source 110, the housing 130, and the ultrasonic transducer 150 of the ultrasonic surgical device 100, respectively. The ultrasonic probe 290 may be an ultrasonic cauterizer. The shape and dimensions of the housing 230 of the ultrasonic surgical pen 200 also provide for a different ergonomic option than the ultrasonic surgical device 100.

Figure 3:
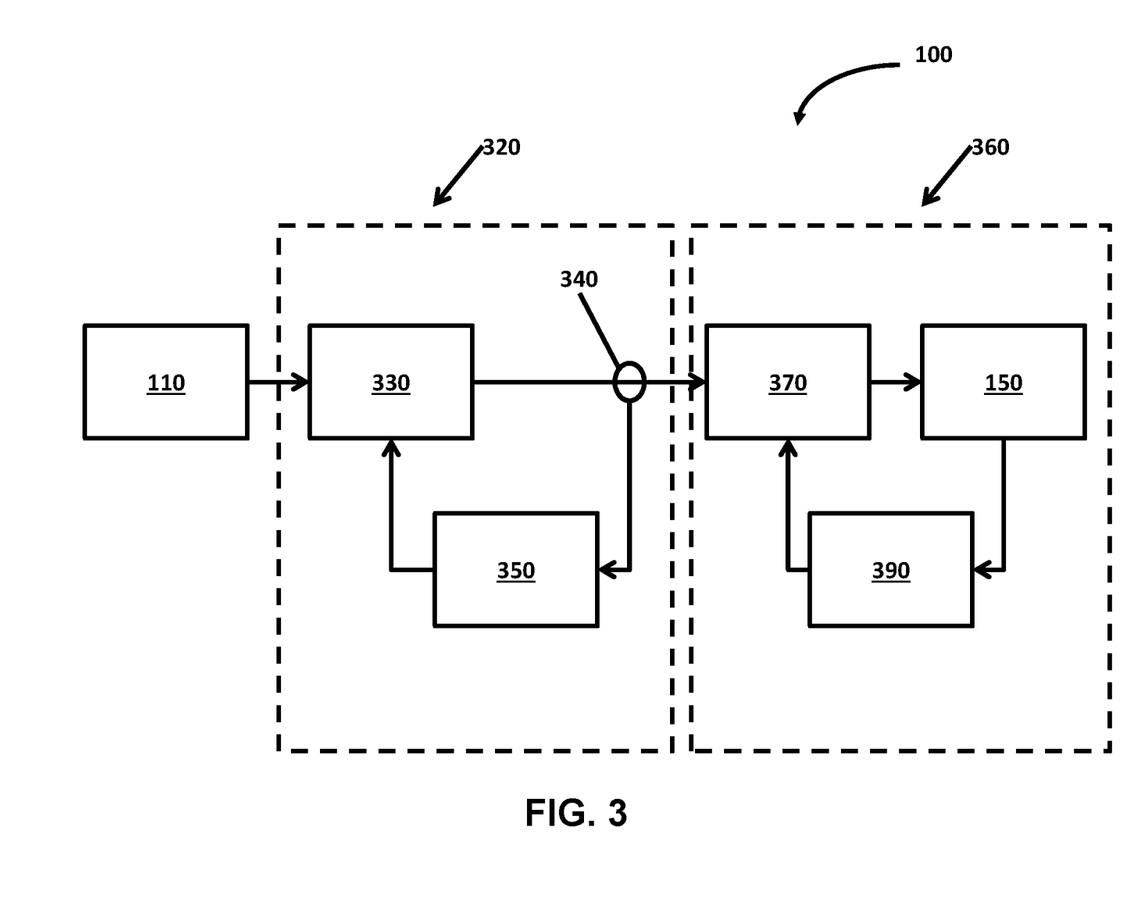
FIG. 3 is a block diagram of the ultrasonic surgical device of FIG. 1A in accordance with embodiments of the present disclosure.

FIG. 3 illustrates a block diagram of the ultrasonic surgical device 100 using a band-pass filter (BPF) oscillator architecture, which tracks the resonant frequency of the BPF regardless of process variations and environmental interferences. A pulse-width modulation (PWM) signal is used to regulate ultrasonic mechanical motion as described in further detail below.

The ultrasonic surgical device 100 includes the power source 110, an amplitude controller 320, and a resonance tracking controller 360. The amplitude controller 320 includes a converter 330, a sensor 340 and a controller 350. The resonance tracking controller 360 includes a non-resonant inverter 370, the ultrasonic transducer 150, and a comparator 390.

The power source 110 provides DC power to the amplitude controller 320, which controls amplitude of output of the amplitude controller 320 so that ultrasonic surgical device 100 generates ultrasonic mechanical motion suitable for treating tissue. In an aspect, when the DC power is provided, the converter 330 amplifies the amplitude of the DC power. The converter 330 may be a buck converter or a step-down converter. The sensor 340 then senses current flowing to the resonance tracking controller 360. The controller 350 receives the sensed results from the sensor 340 and generates a digital pulse width modulated (PWM) control signal to control a duty cycle of the converter 330.

The resonant tracking controller 360 is configured to generate ultrasonic motion at a frequency substantially equal to the resonant frequency of the ultrasonic transducer 150. In an aspect, the non-resonant inverter 370 receives the amplified DC power from the converter 330 and inverts to AC power having a first frequency. The non-resonant inverter 370 is driven by output signals from the comparator 390. The comparator 390 adjusts the frequency of the AC power from the initial (e.g., first) frequency until the frequency is substantially equal to the resonant frequency of the ultrasonic transducer 150. The non-resonant inverter 370 may include any suitable electrical topology such as an H-bridge (e.g., full bridge), a half bridge, and the like.

In an aspect, the output signals from the comparator 390 may be digitally generated by the controller 350. The controller 350 may be a programmable gate array (PGA), field-programmable gate array (FPGA), application-specific integrated circuit (ASIC), complex programmable logic device (CPLD), or any other suitable logic device.

The controller 350 also generates PWM control signals to drive the converter 330 and resonant control signals for the non-resonant inverter 370. The controller 350 receives outputs from the comparator 390 and generates resonant signals for the non-resonant inverter 370 in response to the output of the comparator 390. The non-resonant inverter 370 then inverts the DC power to the AC signal, whose frequency is independent of the switching frequency of the non-resonant inverter 370, by tracking the resonant frequency of the ultrasonic transducer 150.

In an aspect, a transformer (not shown) may be electrically coupled between the non-resonant inverter 370 and the ultrasonic transducer 150 so that the transformer may increase or decrease the amplitude of the inverted AC power to a desired level.

The ultrasonic transducer 150 receives the AC power having a first frequency and generates ultrasonic mechanical motion. In a case when the frequency of the AC signals is different from the resonant frequency of the ultrasonic transducer 150, ultrasonic mechanical motion generated by the ultrasonic transducer 150 may not be optimal for intended purposes. The comparator 390 is configured to track the resonant frequency of the ultrasonic transducer 150 to cause the frequency of the AC signal to match the resonant frequency of the ultrasonic transducer 150 to provide for optimal operation of the ultrasonic transducer 150.

In an aspect, the resonance tracking controller 360 may include a resonant inverter (not shown) connected to the ultrasonic transducer 150 without the non-resonant inverter 370 and the comparator 390. The resonant inverter may be configured to invert the amplified DC signals and generate AC signal having a frequency substantially equal to the resonant frequency of the ultrasonic transducer 150.

In an aspect, the resonant tracking controller 360 may be used to detect a resonant frequency of the ultrasonic transducer 150. The sensor 340 is configured to sense voltage and current of the broadband AC signals applied to the ultrasonic transducer 150 and transmit the sensor signals to the controller 350. The controller 350 digitally processes the sensor signals and monitors the voltage and current values. Further, the controller 350 performs frequency response analysis (e.g., Fourier transformation, digital Fourier transformation, or other frequency related analysis) to identify amplitude response with respect to frequencies of the current. The resonant frequency of the ultrasonic transducer 150 may be a frequency at which the amplitude response of the current is the maximum.

Figure 4:
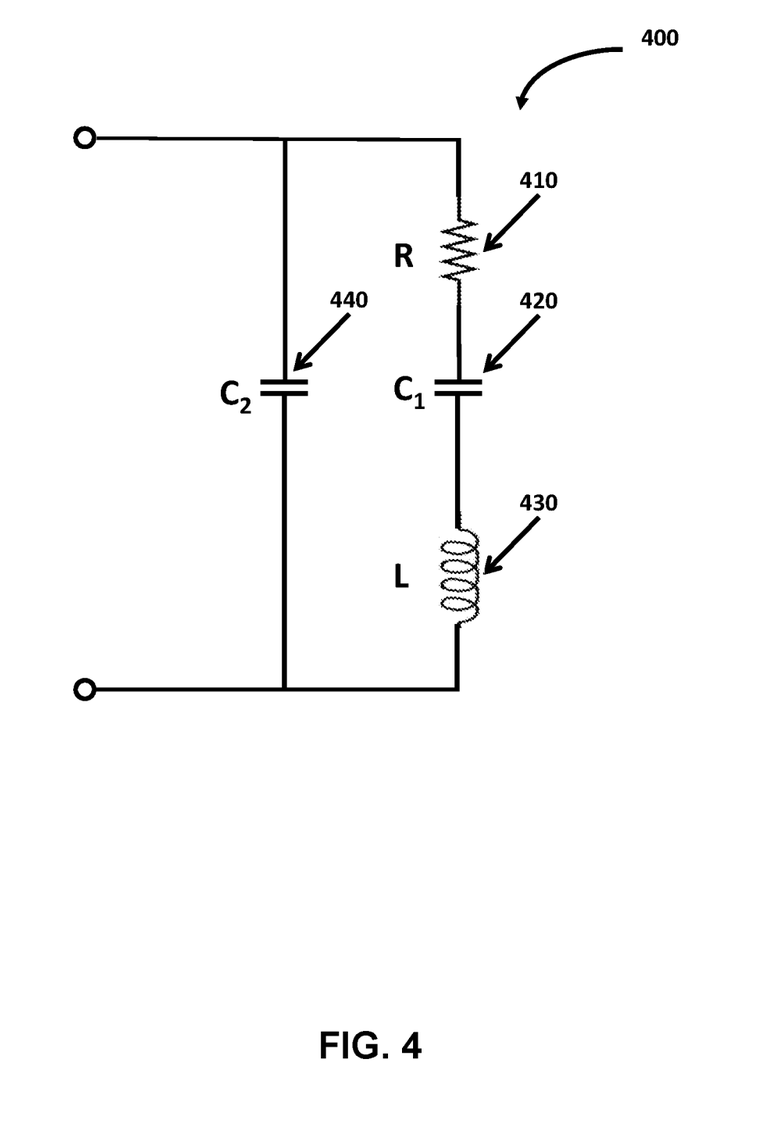
FIG. 4 is a circuit diagram illustrating an electrical circuit model of an ultrasonic transducer or an ultrasonic probe of the ultrasonic surgical device of FIG. 1A in accordance with embodiments of the present disclosure.

FIG. 4 shows an electrical circuit model 400 of the ultrasonic transducer 150 or the ultrasonic probe 190 in accordance with embodiments of the present disclosure. The electrical circuit model 400 models resonant behavior of the ultrasonic transducer 150. The electrical circuit model 400 is a series resistor-inductor-capacitor (RLC) circuit including a resistor 410, a capacitor 420, and an inductor 430, which is parallelly connected with another capacitor 440. In this RLC circuit 400, the resistor 410, the capacitor 420, and the inductor 430 are connected in series with a voltage source. Thus, when the voltage source is connected to the RLC circuit 400, due to the potential difference, a current starts to flow through the RLC circuit 400.

The resonant frequency f of the RLC circuit 400 may be calculated using formula (I) below:

$$f = \frac{1}{2\pi\sqrt{L \cdot C_1}}, \quad (I)$$

where L is the inductance of the inductor 430 and $C_1$ is the capacitance of the capacitor 420. Based on this series model of the RLC circuit 400, the inductance and the capacitance of the ultrasonic transducer 150 determine the resonant frequency of the ultrasonic transducer 150.

The ultrasonic transducer 150 converts electrical energy into mechanical motion fully at the resonant frequency of the ultrasonic transducer 150. In other words, when the ultrasonic transducer 150 is operated at a frequency different from the resonant frequency, the ultrasonic transducer 150 does not operate optimally. Further, when the ultrasonic probe 190 is not properly connected to the ultrasonic transducer 150, the ultrasonic probe 190 cannot deliver the ultrasonic motion to tissue for intended therapeutic purposes.

Generally, the ultrasonic transducer 150 is designed to have a resonant frequency substantially equal to the resonant frequency of the ultrasonic probe 190. In an aspect, the resonant frequency of the ultrasonic transducer 150 or the ultrasonic probe 190 may be obtained by testing and/or during manufacturing. In another aspect, the resonant frequencies may be measured and calculated or identified by the controller 350 of the ultrasonic surgical device 100. Determination of the resonant frequency may be accomplished using the comparator 390 with the non-resonant inverter 370, which can track the resonant frequency. The non-resonant inverter 370 may apply AC signals at a single frequency to the ultrasonic transducer 150 for a predetermined time and the comparator 390 may then track the frequency of the electrical energy until the resonant frequency is identified. The resonant frequency of the ultrasonic probe 190 may also be identified or measured using other techniques known in the related art. A pre-identified resonant frequency of the ultrasonic probe 190 may be used in determining a proper mechanical connection between the ultrasonic transducer 150 and the ultrasonic probe 190.

In an aspect, physical parameters of the ultrasonic probe 190 may be adjustable, when the resonant frequency of the ultrasonic probe 190 is not substantially equal to the resonant frequency of the ultrasonic transducer 150. The length of a waveguide 192 of the ultrasonic probe 190 may be adjusted to match the resonant frequency of the ultrasonic probe 190 to that of the ultrasonic transducer 150.

In an aspect, when the resonant frequency of the combination of the ultrasonic transducer 150 and the ultrasonic probe 190 is offset from the resonant frequency of the ultrasonic transducer 150 from about 1% to about 10% of the resonant frequency, in embodiments, from about 3% to about 7% of the resonant frequency. The offset indicates the ultrasonic transducer 150 is properly connected with the ultrasonic probe 190. Otherwise, the ultrasonic surgical device 100 may display a warning message on the display or generate an alert. The amplitude controller 320 of the ultrasonic surgical device 100 may terminate supply of electrical energy to the ultrasonic transducer 150 to prevent further use.

Figure 5:
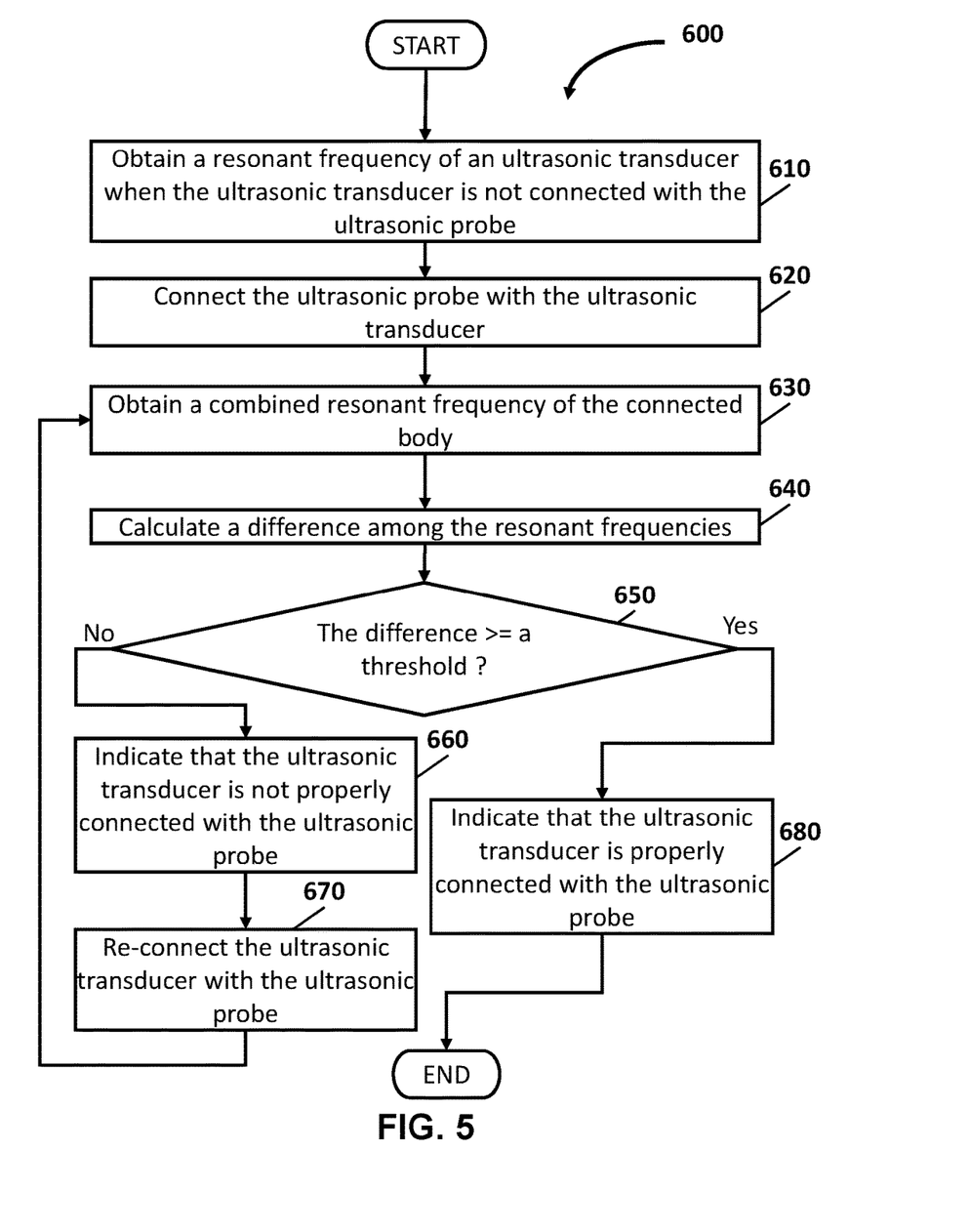
FIG. 5 is a flow chart of a method for analyzing the connection between the ultrasonic transducer and the ultrasonic probe in accordance with embodiments of the present disclosure.

FIG. 6 shows a method 600 for detecting a proper connection between an ultrasonic transducer 150 and the ultrasonic probe 190 in accordance with embodiments of the present disclosure. At step 610, a resonant frequency of the ultrasonic transducer 150 may be obtained. In an aspect, the resonant frequency of the ultrasonic probe 190 may be pre-identified and can be used.

In an aspect, a controller of the ultrasonic surgical device 100 may identify or calculate resonant frequencies by applying AC signals to the ultrasonic transducer 150 for a predetermined time, when the ultrasonic probe 190 is not coupled to the ultrasonic transducer 150. The controller 350 then measures the voltage and current of the ultrasonic transducer 150, and calculates or identifies the resonant frequency of the ultrasonic transducer 150 by identifying a frequency at which amplitude response of the current is at its maximum. After the resonant frequency is obtained, in step 620, the ultrasonic probe 190 is coupled to the ultrasonic transducer 150 via the locking portion 162 of FIG. 1B.

In step 630, a combined frequency of the connected body 510 of the ultrasonic transducer 150 and the ultrasonic probe 190 is obtained. Since the connected body 510 is a combined structure, the resonant frequency of the connected body 510 may be different from those of the ultrasonic transducer 150 or the ultrasonic probe 190.

In step 640, difference between the resonant frequencies of the ultrasonic transducer 150 and the connected body 510 are calculated and in step 650. The difference is compared with a predetermined threshold value to determine if there is a substantial difference between resonant frequencies, which is indicative of the ultrasonic probe 190 being attached to the ultrasonic transducer 150. If the difference is greater than or equal to the predetermined threshold value, the method 600 proceeds to step 680, in which a message indicating that the ultrasonic probe 190 is properly connected with the ultrasonic transducer 150 is displayed on the output device 180 of the ultrasonic surgical device 100, allowing the clinician to use the ultrasonic surgical device 100.

In an aspect, in step 640, the pre-identified resonant frequency of the ultrasonic probe 190 may be used instead of that of the ultrasonic transducer 150. That is a difference between the resonant frequencies of the ultrasonic probe 190 and the connected body 510. In step 650, the difference is compared with the predetermined threshold value.

In a case when the difference is less than the predetermined threshold value, namely, the difference is insubstantial, in step 660, a warning message may be displayed on the output device 180 of the ultrasonic surgical device 100, indicating that the ultrasonic probe 190 is not properly connected to the ultrasonic transducer 150. In an aspect, the output device of the ultrasonic surgical device 100 may be a speaker and generate an audible alert. In another aspect, the ultrasonic surgical device 100 may terminate supply of electrical energy to the ultrasonic transducer 150 to prevent potential malfunction. In embodiments, a replacement ultrasonic probe may be used to troubleshoot the connection to the ultrasonic transducer 150.

After displaying the warning message or outputting an alert, the ultrasonic probe 190 may be re-connected with the ultrasonic transducer 150 in step 670. After step 670, the method 600 repeats steps 630-670 until all the differences are less than the predetermined threshold value or the ultrasonic probe 190 is properly connected with the ultrasonic transducer 150.

In an aspect, step 670 may include changing physical property of the ultrasonic probe 190, when the combined resonant frequency is much lower than the resonant frequency of the ultrasonic transducer 150 and/or the ultrasonic probe 190. The length of the waveguide 192 of the ultrasonic probe 190 may be shortened. The length of the waveguide 192 of the ultrasonic probe 190 may be lengthened in response to the combined resonant frequency being higher than the resonant frequency of the ultrasonic transducer 150 and/or the ultrasonic probe 190. In this way, the combined resonant frequency can be adjusted to match the resonant frequencies of the ultrasonic transducer 150 and/or the ultrasonic probe 190. The waveguide 192 may be telescopic to allow for longitudinal adjustment.

In another aspect, step 670 may include changing physical property of the ultrasonic probe 190 when the difference between the resonant frequencies of the ultrasonic transducer 150 and/or the ultrasonic probe 190 is greater than the predetermined threshold value. By shortening or lengthening the length of the waveguide 192 of the ultrasonic probe 190, the resonant frequency of the ultrasonic probe 190 may be matched to the resonant frequency of the ultrasonic transducer 150.

In a further aspect, the method 600 may be terminated after a predetermined number of attempts to couple the ultrasonic probe 190 to the ultrasonic transducer 150. In embodiments, when the ultrasonic probe 190 is re-connected to the ultrasonic transducer 150 five times or more and the difference between the resonant frequency of the ultrasonic transducer 150 and the combined resonant frequency is still greater than the predetermined threshold value, the method 600 may display a termination message and terminate the method 600. The termination message may indicate that incurable defects may be present in the ultrasonic probe 190, the ultrasonic transducer 150, or the ultrasonic surgical device 100 and thus even proper connection between the ultrasonic probe 190 and the ultrasonic transducer 150 cannot produce desired ultrasonic motion.

In a still further aspect, when the length of the waveguide 192 of the ultrasonic probe 190 is adjusted more than a predetermined number of times (e.g., five times or more) and any the difference is larger than the predetermined threshold value, the method 600 may display the termination message and terminate the method 600.

Since other modifications and changes may be made to fit particular operating requirements and environments, it is to be understood by one skilled in the art that the present disclosure is not limited to the illustrative examples described herein and may cover various other changes and modifications which do not depart from the spirit or scope of this disclosure.

What is claimed is:

1. An ultrasonic surgical device comprising:
   a power source configured to generate power;
   an ultrasonic transducer having a first resonant frequency, the ultrasonic transducer electrically coupled to the power source and configured to generate ultrasonic motion in response to the generated power;
   an ultrasonic probe configured to be mechanically couplable to the ultrasonic transducer, the ultrasonic transducer and the ultrasonic probe having a second resonant frequency when the ultrasonic probe is coupled to the ultrasonic transducer; and a controller configured to make a determination of whether the ultrasonic probe is properly coupled to the ultrasonic transducer based on the first resonant frequency and the second resonant frequency, to calculate a difference between the first resonant frequency and the second resonant frequency, to determine whether the ultrasonic probe is properly coupled to the ultrasonic transducer based on a comparison of the difference and a predetermined threshold, and to determine that the ultrasonic probe is properly coupled to the ultrasonic transducer based on the difference being above the predetermined threshold.

2. The ultrasonic surgical device according to claim 1, wherein the power source includes:
   a battery configured to generate a direct current (DC) power; and
   an inverter electrically coupled to the battery and configured to invert the DC power to an alternating current (AC) power having an ultrasonic frequency.

3. The ultrasonic surgical device according to claim 1, wherein the power source further includes:
   an alternating current (AC) power source configured to supply AC power having a low frequency;
   a converter configured to convert the AC power to a direct current (DC) power;
   an amplifier configured to amplify an amplitude of the DC power; and
   an inverter configured to invert the amplified DC power to an AC power having an ultrasonic frequency.

4. The ultrasonic surgical device according to claim 1, further comprising a display configured to display a warning in response to the determination of proper coupling between the ultrasonic probe and the ultrasonic transducer.

5. The ultrasonic surgical device according to claim 4, further comprising an audio output port configured to output an audible alert in response to the determination of proper coupling between the ultrasonic probe and the ultrasonic transducer.

* * * * *